(12) United States Patent
Han et al.

(10) Patent No.: US 11,672,467 B2
(45) Date of Patent: *Jun. 13, 2023

(54) USER DEVICE BASED PARKINSON'S DISEASE DETECTION

(71) Applicant: TENCENT AMERICA LLC, Palo Alto, CA (US)

(72) Inventors: Lianyi Han, Palo Alto, CA (US); Hui Tang, Mountain View, CA (US); Yusheng Xie, Mountain View, CA (US); Shih-Yao Lin, Palo Alto, CA (US); Qian Zhen, Santa Clara, CA (US); Zhimin Huo, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,577

(22) Filed: May 6, 2022

(65) Prior Publication Data

US 2022/0257171 A1    Aug. 18, 2022

Related U.S. Application Data

(63) Continuation of application No. 16/554,006, filed on Aug. 28, 2019, now Pat. No. 11,375,945.

(51) Int. Cl.
*A61B 5/00* (2006.01)
*A61B 5/11* (2006.01)

(52) U.S. Cl.
CPC .......... *A61B 5/4082* (2013.01); *A61B 5/1112* (2013.01); *A61B 5/1114* (2013.01); *A61B 5/0022* (2013.01); *A61B 5/1101* (2013.01); *A61B 5/681* (2013.01); *A61B 2562/0219* (2013.01)

(58) Field of Classification Search
CPC ... A61B 5/4082; A61B 5/1112; A61B 5/1114; A61B 5/0022; A61B 5/1101; A61B 5/681; A61B 2562/0219; A61B 5/0077; A61B 5/0082; A61B 5/112; A61B 2505/09; A61B 5/4064; A61B 5/6898; A61B 5/7264; A61B 5/7275; A61B 5/7282

See application file for complete search history.

(56) References Cited

U.S. PATENT DOCUMENTS

| | | |
|---|---|---|
| 2011/0102568 A1 | 5/2011 | Bonnet |
| 2014/0257047 A1 | 9/2014 | Sillay |
| 2018/0338710 A1 | 11/2018 | Tas et al. |
| 2019/0142328 A1 | 5/2019 | Broderick et al. |

OTHER PUBLICATIONS

Written Opinion of the International Searching Authority in International Application No. PCT/US2020/045177 dated Oct. 21, 2020.
International Search Report in International Application No. PCT/US2020/045177 dated Oct. 21, 2020.

*Primary Examiner* — Patrick Fernandes
*Assistant Examiner* — Joseph A Tombers
(74) *Attorney, Agent, or Firm* — Sughrue Mion, PLLC

(57) ABSTRACT

A method and user device for determining a unified Parkinson's disease rating scale (UPDRS) value associated with a user of the user device include obtaining video data associated with a movement of a body part of the user. The UPDRS value is determined using a model and the video data associated with the movement of the body part of the user. The UPDRS value is provided to permit an evaluation of the user based on the UPDRS value.

20 Claims, 5 Drawing Sheets

USER DEVICE BASED PARKINSON'S DISEASE DETECTION

CROSS-REFERENCE TO RELATED APPLICATIONS

This application is a continuation of U.S. application Ser. No. 16/554,006 filed Aug. 28, 2019.

BACKGROUND

Parkinson's disease is a long-term and progressive central nervous system disorder that mainly affects the motor system. Motor related symptoms start gradually, often with a barely noticeable tremor in just one hand, and gradually worsen overtime. At an early stage of Parkinson's disease, motor related symptoms such as tremors, shaking, slowness of movement, rigidity, etc. are very common. At later stages, and as the disease progress, non-motor symptoms may occur. A patient may experience walking difficulties, and thinking and behavior related symptoms such as sensory difficulties, sleep disorder, and emotional problems. Briefly, motor problems are collectively a main symptom of Parkinson's disease. The evaluation of the disease stages and symptoms has been a main focus in the clinical practice. The motor problems can be reflected in other forms of motion disorders such as, for example, stiffness and lagging in the movement of the patient's extremities, which can be qualified by analyzing videos that capture patient's motion.

SUMMARY

According to an aspect of the disclosure, a method performed by a user device for determining a unified Parkinson's disease rating scale (UPDRS) value associated with a user of the user device, includes obtaining, by a processor of the user device, video data associated with a movement of a body part of the user; determining, by the processor of the user device and using a model, the UPDRS value based on the video data associated with the movement of the body part of the user, after obtaining the video data associated with the movement of the body part of the user; and providing, by the processor of the user device, the UPDRS value, after determining the UPDRS value, to permit an evaluation of the user based on the UPDRS value.

According to an aspect of the disclosure, a user device comprises at least one memory configured to store program code; and at least one processor configured to read the program code and operate as instructed by the program code, the program code including obtaining code configured to cause the at least one processor to obtain video data associated with a movement of a body part of the user; determining code configured to cause the at least one processor to determine, using a model, the UPDRS value based on the video data associated with the movement of the body part of the user, after obtaining the video data associated with the movement of the body part of the user; and providing code configured to cause the at least one processor to provide the UPDRS value, after determining the UPDRS value, to permit an evaluation of the user based on the UPDRS value.

According to some possible implementations, a non-transitory computer-readable medium stores instructions, the instructions include one or more instructions that, when executed by one or more processors of a device, cause the one or more processors to obtain video data associated with a movement of a body part of the user; determine, using a model, the UPDRS value based on the video data associated with the movement of the body part of the user, after obtaining the video data associated with the movement of the body part of the user; and provide the UPDRS value, after determining the UPDRS value, to permit an evaluation of the user based on the UPDRS value.

DETAILED DESCRIPTION

Figure 1:
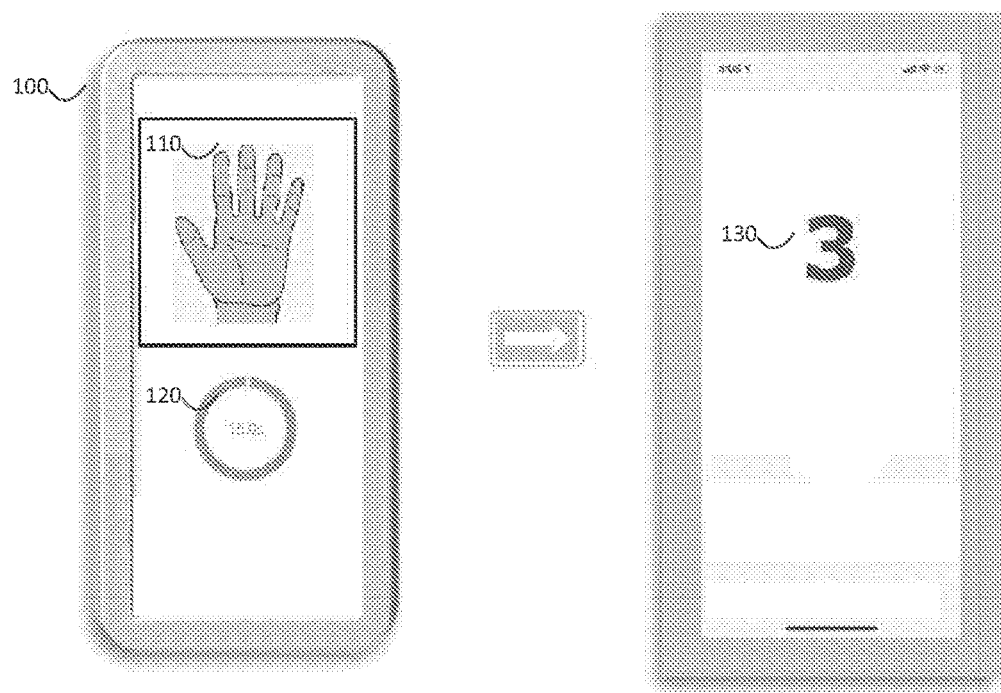
FIG. 1 is a diagram of an overview of an example implementation described herein.

In 2015, 6.2 million people were affected by Parkinson's disease, which also lead to 117,400 deaths globally. Parkinson's disease is often seen in people over 60 years of age with about 1% of the population being affected. The average life expectancy following diagnosis is between 7 and 14 years. The cost of Parkinson's disease to society is high, and Parkinson's disease reduces the quality of life of those afflicted with the disease and their caregivers. Therefore, the present disclosure utilizes the motion sensor(s) of a user device to monitor the progress of the movement in relation to Parkinson's disease, thereby assisting patients and their caregivers with an easy to reach, and simple to use health monitoring tool.

Recent advances in sequential data analysis using deep neural network (DNN) approaches have made significant progress. Additionally, the popularity of powerful mobile devices has reached a point where artificial intelligence (AI) based applications can be accessible by a majority of the general public. The present disclosure, by permitting a user device to be utilized as an assistive medical diagnosis tool, will attempt to preliminarily screen for signs of motion related Parkinson's disease symptoms. The present disclosure permits, among other things, the following benefits: evaluation of Parkinson's disease motion related symptoms; provision of multiple categories of motion testing with the scale of 0-4 as in the Unified Parkinson Disease Rating Scale (UPDRS) clinical testing; and provision of a mobile application that is easy to install without additional hardware requirements of user devices.

A medical diagnosis assistive application of the present disclosure is configured to quantitatively measure the disease state of Parkinson's disease patients regularly. Motion sensors such as accelerometers, gyroscopic sensors, and/or the like have been effectively imbedded within most modern user devices, such as mobile phones, smart watches, etc.

Multiple dimensional motion data is able to measure the movement of the body that is closely attached to the user device, at a 10 to 50 Hz sampling rate which is sufficient to quantitatively measure the Parkinson's disease patient's motor function. Especially in recent years, the advances in DNNs and the Long Short Term Memory Network (LSTM) shows promising results in analyzing time series data, thereby empowering the possibility of making more accurate AI-based Parkinson's disease motion analysis.

The present disclosure addresses the following challenges: (1) tradeoff between the misdiagnosis and false positives; (2) the architecture of the frontend and backend that communicate through an AI-based data analysis processing pipeline.

The present disclosure addresses the technical barrier regarding providing advanced AI-powered technology to reality, and provides a practical application that is accessible, and easy to use. The present disclosure separates the AI service and the client application into their own self-independent and loosely coupled components. The separation of the AI service and the client sensor collection modules allows the multiple components to be developed, tested, and deployed in the parallel. In addition, and with this configuration, user devices may conserve processing and hardware resources by dispensing with the need to perform computationally expensive calculations where the computation power and capability of the user device can be a constraining factor. Since the user device executing the client-side application is able to perform motion testing and data collection, the user is able to gain the flexibility of performing the testing at a convenient location, such as homecare environment.

The present disclosure is directed towards a practical application that permits accurate and real-time testing by user devices.

The proposed disclosure provides a preliminary screening tool for early detection of Parkinson's disease by evaluating motor functions. Further, the present disclosure permits the monitoring of Parkinson's disease states regularly for better patient care and management. According to a first scenario of the present disclosure, a health care professional is able to evaluate Parkinson's disease using an UPDRS scoring system quantitatively, and chronically if needed. According to another scenario of the present disclosure, a user may perform assessments of early signs of motor function disorders periodically.

The model is an end-to-end deep learning model using Unidirectional LSTM-based DNN that utilizes motion sensor time series data in sequential order.

The application architecture follows the model-view-viewmodel (MVVM), where the data model is different than the above mentioned DNN model. The DNN model is utilized for inference during the application life cycle, and communication is provided between the data model and DNN model, where both will feed to the viewer model. The viewer model is configured to serve the user interface (UI) though the data binding. The DNN model can be stored on the cloud and/or locally on mobile devices.

The motion sensor data is recorded in real time with an adjustable rate, as an example, of 10 hz-50 hz, and it can be analyzed locally on the user device or remotely through cloud services. As examples, the score of 0-4 will be provided after the sensor data is evaluated. This score is correlated to the MDS-UPDRS, a Parkinson Motor Rating Scale which is for Parkinson disease state evaluation.

According to an embodiment, a system collects sensor data and analyzes the sensor data to determine the severity of tremor or shaking corresponding to the UPDRS scale.

According to an embodiment, a system captures video data of motion of certain hand movements or motions of other body part movements from a patient under guided instructions and analyzes the pattern of the motions to determine the severity of motion disorders of individual movements corresponding to the UPDRS scale for a given movement.

According to an embodiment, a system captures sensor data and captures video data of motion of certain hand movements or motions of other body part movements from a patient under guided instructions. The captured sensor data and/or video data are analyzed to determine the severity of the individual's motion disorders of individual movements corresponding to the UPDRS scale for a given movement. Further, the system may use all or select movements to predict the overall UPDRS score to determine the stage of Parkinson's disease for the patient.

According to an embodiment, a system uses a model to predict the overall UPDRS score or the stage of Parkinson's disease using a subset of movements from the analysis of video or sensor data.

According to an embodiment, the sensor data is recorded with the user device's built-in gyroscopic sensor and accelerometer with the guidance of predefined gestures and movements.

The quantitative and continuous monitoring of Parkinson's disease has remained a challenge for Parkinson's disease caregivers. The present disclosure permits patient management with an easy to reach and simple to use application that makes health monitoring possible and convenient.

The present disclosure provides insights for improved treatment plans and ultimately improves the quality of life for Parkinson's disease patients. The present disclosure provides an AI-based mobile application that users may utilize to evaluate motor functions for pre-screening of Parkinson's disease. The success of the DNN model can further extent the app for facilitating a comprehensive diagnosis. The MVVM design of the app can be adopted to deliver better DNN models overtime, eventually make the mobile device as a reliable and easy to use health monitoring tool that able to fill the emerging market for online diagnosis.

FIG. 1 is a diagram of an overview of an embodiment described herein. As shown in FIG. 1, a user device 100 (e.g., a mobile phone) may determine a unified Parkinson's disease rating scale (UPDRS) value associated with a user of the user device 100. For example, the user device 100 may execute an application that permits the user device 100 to determine a UPDRS value associated with a user that is manipulating the user device 100.

The user may correspond to a person that is being tested for Parkinson's disease, that is being monitored or evaluated for Parkinson's disease, and/or the like. In this case, the user device 100 may execute the application that permits evaluation of the user by determining a UPDRS value for the user.

As shown in FIG. 1, the user device 100 (e.g., a processor of the user device 100) may obtain video data 100 associated with a movement of a body part of the user. The video data may permit the user device to determine the UPDRS value, as described in more detail below. The user device 100 may obtain the video data using a camera of the user device 100.

First, and in some cases, the user device 100 may provide, via an output component (e.g., a display, a speaker, etc.), a prompt that instructs the user to perform a predetermined gesture using a body part of the user. For example, the prompt may instruct the user to move the user's hand in a predefined manner. As another example, the prompt may instruct the user to maintain the user's hand in a still position. As another example, the prompt may instruct the user to move the user's arm in a particular motion. It should be understood that the body part of the user may include any body part of the user and/or any combination of body parts of the user. Further, it should be understood that the predetermined gesture may include any type of gesture. Alternatively, the prompt may instruct the user to perform any particular motion or gesture. That is, the user may move the body part (or maintain a still position) in any un-predefined way.

The user device 100 may also prompt the user to record, using the user device 100, video data of the body part while the user performs the movement of the body part. Accordingly, the user may manipulate the user device 100 to obtain video data of the body part of the user while the user performs the movement of the body part.

As further shown in FIG. 1, the user device 100 (e.g., the processor of the user device 100) may determine whether a measurement condition 120 is satisfied. For example, the measurement condition may correspond to a threshold amount of time having elapsed since the beginning of the obtaining of video data, to a threshold amount of video data being obtained, to the movement of the body part having been completed, to a number of predetermined movements or gestures having been performed, to a set of prompts being completed, to a threshold amount of video data needed for accurate UPDRS value determination having been obtained, and/or the like.

As further shown in FIG. 1, the user device 100 (e.g., the processor of the user device 100) may determine, using a deep neural network (DNN) model. For example, the user device 100 may input the video data and/or processed video data into a DNN model, and determine a UPDRS value 130 based on an output of the model. The UPDRS value 130 may include a movement disorder society (MDS) UPDRS value, and may include a value from one, two, three, four, etc.

In some implementations, the user device 100 may input the raw video data into the model, and determine the UPDRS value 130 based on an output of the model. Alternatively, the user device 100 may perform one or more video processing techniques, may input processed video data into the model, and determine the UPDRS value 130 based on an output of the model.

The user device 100 may receive a trained model from a cloud-based platform (e.g., server), and store the model. In this way, the user device 100 may conserve processor and/or memory resources by reducing the need to perform computationally expensive calculations. The cloud-based platform may utilize machine learning techniques to analyze data and generate models. For instance, the cloud-based platform may analyze millions, billions, trillions, etc. of data points, and generate models that correlate video data and UPDRS values. In this way, user device 100 may receive the model, and utilize the model in association with the application that permits determination of a UPDRS value 130.

As further shown in FIG. 1, the processor of the user device 100 may provide the UPDRS value 130 to permit an evaluation of the user based on the UPDRS value 130. For example, the user device 100 may provide, via an output component (e.g., a user interface), information that identifies the UPDRS value 130 to permit the user, physician, caregiver, medical personnel, etc. to identify the UPDRS value.

In other cases, the user device 100 may provide the UPDRS value 130 to a set of other devices via a network in real time. In some implementations, the user device 100 may provide the UPDRS value 130 in a standardized format to permit various databases and records to be updated based on the UPDRS value.

The user device 100 may standardize the UPDRS value 130 using a standardization technique, such that the set of devices may each utilize the UPDRS value 130.

The user device 100 may collect medical information of the user, and convert and consolidate the medical information into a standardized format. Further, the user device 100 may generate the UPDRS value 130 in association with a standardized format. The user device 100 may store the standardized UPDRS value 130 in a set of network-based storage devices (e.g., a cloud-based platform), and generate messages notifying health care providers, doctors, medical personnel, patients, etc. whenever the UPDRS value is generated, updated, etc.

Further, the user device 100 may provide the UPDRS value 130 to the set of devices in real time (e.g., substantially concurrently with the generation of the UPDRS value 130) to permit the set of devices to update and/or utilize the UPDRS value 130 in real time. In this way, various users of the set of devices may have immediate access to up-to-date UPDRS values 130 of the user.

In this way, and as compared to non-standardized medical information associated with different medical providers, some implementations herein permit standardized medical information and/or UPDRS values 130 to be generated and provided to multiple different devices in real time, thereby allowing different users to share medical information and/or UPDRS values 130.

Further still, and in this way, some implementations herein permit complete and accurate medical information and/or UPDRS values 130 to be provided in real time. As compared to situations where multiple disparate medical personnel have incomplete or inaccurate medical or diagnosis information, some implementations herein permit complete and accurate medical information and UPDRS values 130 to be disseminated and readily-shared between medical personnel.

Figure 2:
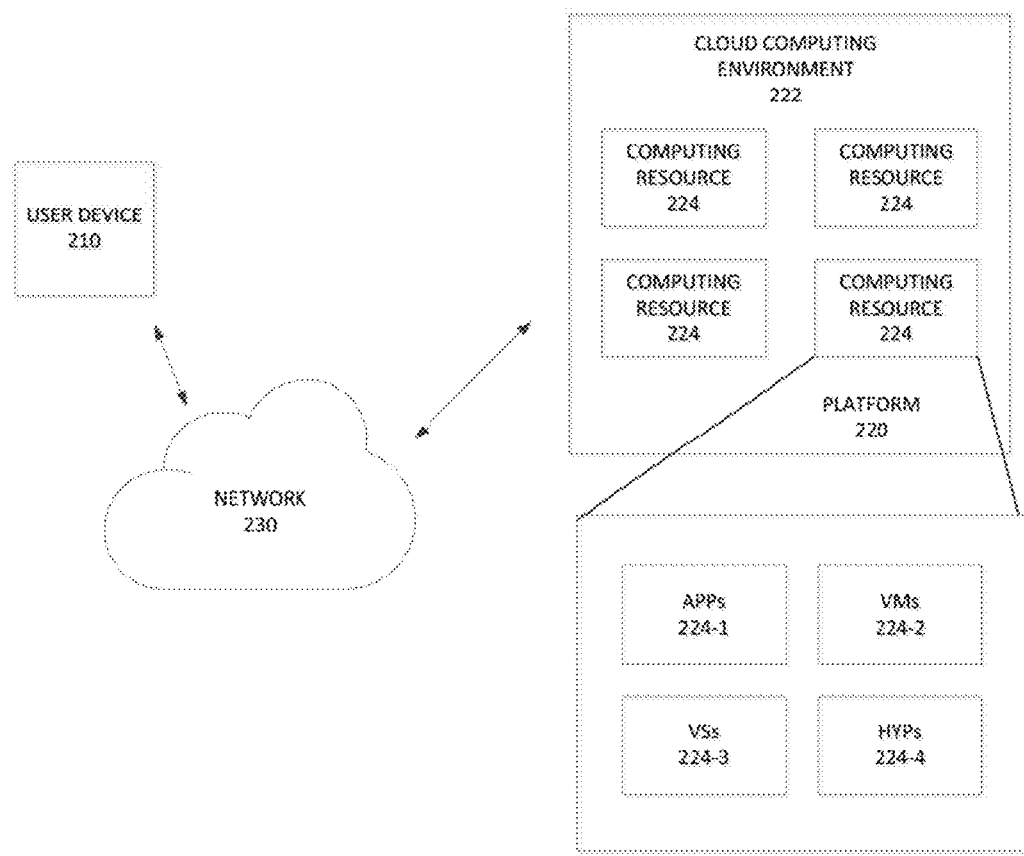
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of determining a unified Parkinson's disease rating scale (UPDRS) value associated with a user of the user device, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
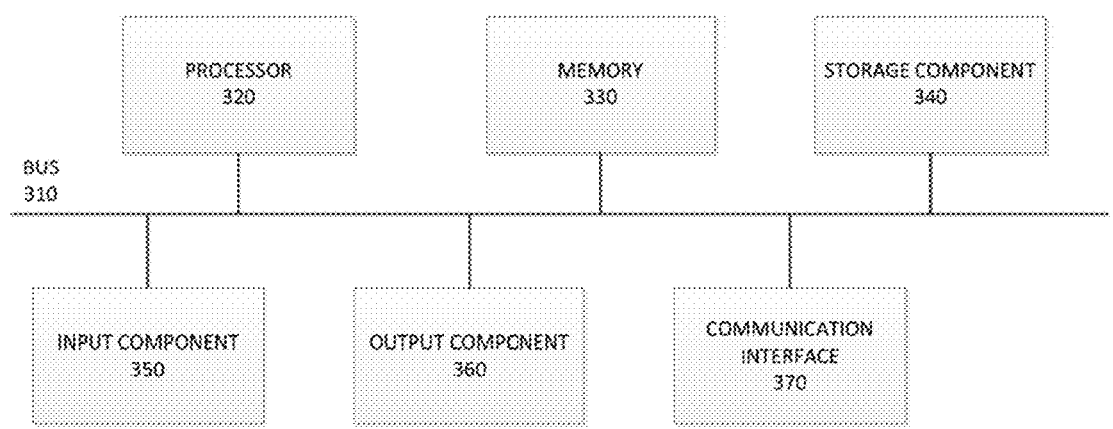
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
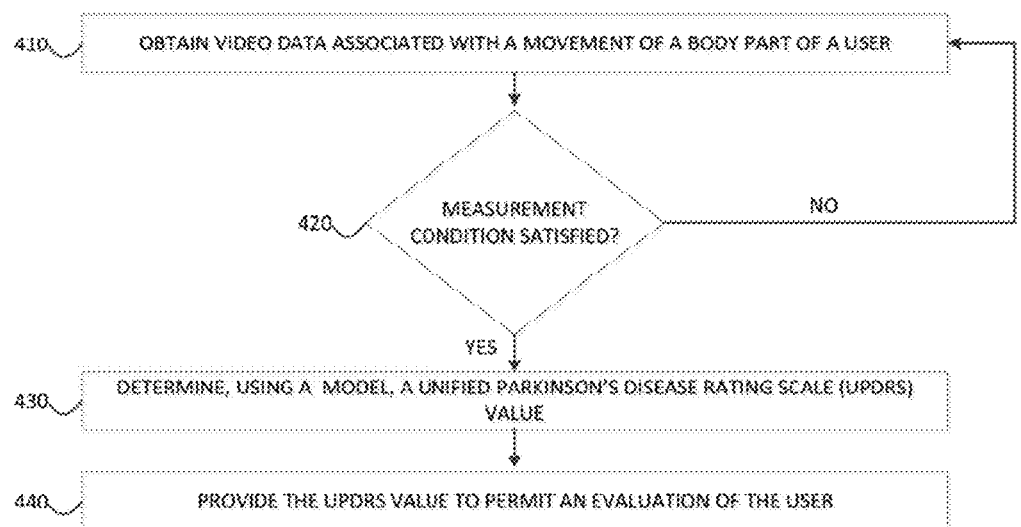
FIG. 4 is a flow chart of an example process for determining a unified Parkinson's disease rating scale (UPDRS) value associated with a user of a user device.

FIG. 4 is a flow chart of an example process 400 for determining a unified Parkinson's disease rating scale (UPDRS) value associated with a user of a user device. In some implementations, one or more process blocks of FIG. 4 may be performed by user device 210. In some implementations, one or more process blocks of FIG. 4 may be performed by another device or a group of devices separate from or including user device 210, such as platform 220.

As shown in FIG. 4, process 400 may include obtaining, by a processor of the user device, video data associated with a movement of a body part of the user (block 410).

For example, user device 210 may obtain video data associated with a movement of a body part of the user in order to determine a UPDRS score. In some implementations, user device 210 may obtain the video data using a camera of the user device 210. That is, a single user device 210 may obtain the video data. Additionally, or alternatively, user device 210 may obtain the video data from another user device 210. That is, multiple user devices 210 may be used to obtain the video data. As an example, a set of fixed, or movable, user devices 210 may obtain video data of the user.

In some implementations, user device 210 may obtain the video data that is of a particular angle. For example, the user device 210 may obtain video data relative to the body part of the user at a particular angle. Additionally, or alternatively, user device 210 may obtain the video data that is of multiple angles relative to the body part of the user. For example, user device 210 may be moved to obtain video data of multiple angles of the body part of the user. As an alternative, multiple user devices 210 that are disposed at different capturing angles relative to the body part of the user may obtain respective video data that is disposed at different angles relative to the body part of the user.

In some implementations, user device 210 may obtain video data of a body part of interest of the user. For instance, the user device 210 may obtain video data of a hand of the user, a finger of the user, an arm of the user, a leg of the user, a torso of the user, a head of the user, a leg of the user, a foot of the user, an entire body of the user, etc.

In some implementations, user device 210 may provide, via an output component, a prompt that instructs the user to perform a predetermined motion. For example, the prompt may instruct the user to perform a predefined motion with the user's hand. As another example, the prompt may instruct the user to walk in a predetermined manner. As another example, the prompt may instruct the user to perform a repetitive motion such as tapping a finger.

In some implementations, user device 210 may perform an image processing technique using the video data. For example, and referring to FIG. 5, the user device 210 may obtain video data associated with a movement of a body part of a user (step 510). Further, the user device 210 may perform image segmentation in order to segment the video data of the body part of the user into segments (step 520). The user device 210 may perform an image segmentation technique, an edge detection technique, a computer vision technique, and/or the like.

In this way, the user device 210 may analyze a subset of the video data, that specifically corresponds to a body part of interest of the user, when determining the UPDRS score as described elsewhere herein. Accordingly, the accuracy of the UPDRS score is improved.

In this way, user device 210 may obtain video data, and utilize the video data to determine a UPDRS score as described below.

As further shown in FIG. 4, process 400 may include determining, by a processor of the user device, whether a measurement condition is satisfied (block 420).

For example, user device 210 may determine whether a measurement condition is satisfied in order to obtain sufficient video data for determining the UPDRS score. The measurement condition may correspond to a threshold amount of time, a threshold amount of video data, a predetermined motion being performed, the video data being of threshold image quality, a waveform of the video data satisfying a threshold, a body part of interest being identified, segmented, labeled, or the like, and/or the like.

As further shown in FIG. 4, if the measurement condition is not satisfied (block 420—NO), then process 400 may include obtaining additional video data (return to block 410).

As further shown in FIG. 4, if the measurement condition is satisfied (block 420—YES), then process 400 may include determining, by the processor of the user device and using a model, the UPDRS value based on the video data associated with the movement of the body part of the user (block 430).

In some implementations, the user device 210 may determine the UPDRS score based on the video data and a model. For example, the user device 210 may input, to the model, the video data, and obtain the UPDRS score based on an output of the model.

As an alternative, the user device 210 may convert the video into another format of data, and determine the UPDRS score based on the converted data. For example, the user device 210 may convert the video data into two dimensional data. As an example, the data may correspond to frequency data of a movement of the body part of the user (e.g., frequency versus time). In some implementations, the user device 210 may determine the UPDRS score based on analyzing the frequency of the movement of the body part of the user, an amplitude of the movement of the body part of the user, and/or the like.

Figure 5:
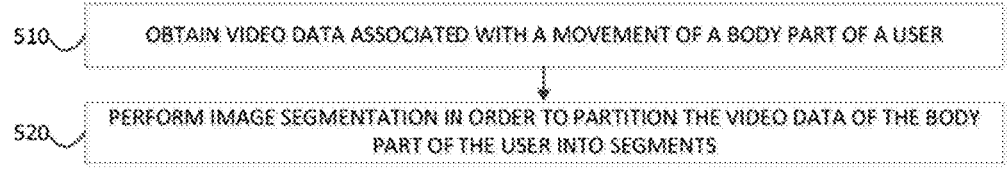
FIG. 5 is a flow chart of an example process for performing an image segmentation technique.

As another alternative, the user device 210 may identify a subset of the video that corresponds to the body part of interest of the user, based on performing the image segmentation technique of FIG. 5. Further, the user device 210 may determine the UPDRS score based on the subset of the video data.

In any event, the user device 210 may determine a UPDRS score based on the video data, and provide the score as described below.

As further shown in FIG. 4, process 400 may include providing, by the processor of the user device, the UPDRS value to permit an evaluation of the user based on the UPDRS value (block 440).

For example, user device 210 may provide, for output, the UPDRS score to permit a user to identify the score.

In some implementations, the user device 210 may provide, for display, the UPDRS score.

As another alternative, the user device 210 may provide, for output, data that corresponds to the video data. For example, the user device 210 may provide a waveform of a movement of the body part of the user. In this case, the user device 210 may display an amplitude of the movement of the body part of the user versus time, a frequency of the movement of the body part of the user versus time, and/or the like. The user device 210 may provide any of the foregoing data along with the UPDRS score as an output. Alternatively, the user device 210 may provide any of the foregoing data as an output instead of the UPDRS score. Accordingly, it should be understood that the user device 210 may provide any of the foregoing data, and/or permutations thereof, as an output.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method performed by a user device for determining a unified Parkinson's disease rating scale (UPDRS) value associated with a user of the user device, comprising:
    providing, via an output component of the user device, a set of prompts, each prompt instructing the user to perform a predefined gesture of a body part;
    obtaining, by a processor of the user device, video data associated with a movement of the body part of the user;
    determining, by the processor of the user device, whether a measurement condition is satisfied, the measurement condition including whether gestures instructed by the set of prompts being completed, a threshold amount of the video data obtained, the video data being of a threshold image quality, a waveform of the video data satisfying a threshold, and the body part in the video data being identified, segmented, and labeled;
    based on the measurement condition being satisfied, determining, by the processor of the user device and using a model, the UPDRS value based on the video data associated with the movement of the body part of the user; and
    providing, by the processor of the user device, the UPDRS value, after determining the UPDRS value, to permit an evaluation of the user based on the UPDRS value.

2. The method of claim 1, further comprising:
    generating, by a sensor of the user device, sensor data based on the user of the user device manipulating the user device; and
    determining the UPDRS value based on the sensor data and the video data.

3. The method of claim 1, further comprising:
determining a stage of Parkinson's disease for the user based on the video data; and
providing information that identifies the stage of Parkinson's disease.

4. The method of claim 1, wherein the UPDRS value is a movement disorder society (MDS) UPDRS value.

5. The method of claim 1, wherein the UPDRS value is at least one of a zero, one, two, three, or four.

6. The method of claim 1, further comprising:
receiving, from a server device, the model that is a deep neural network (DNN) model.

7. The method of claim 1, further comprising:
obtaining a plurality of pieces of video data based on providing the set of prompts.

8. A user device for determining a unified Parkinson's disease rating scale (UPDRS) value associated with a user of the user device, comprising:
at least one memory configured to store program code;
at least one processor configured to read the program code and operate as instructed by the program code, the program code including:
providing code configured to cause the at least one processor to provide, via an output component of the user device, a set of prompts, each prompt instructing the user to perform a predefined gesture of a body part; and
obtaining code configured to cause the at least one processor to obtain video data associated with a movement of the body part of the user;
first determining code configured to cause the at least one processor to determine whether a measurement condition is satisfied, the measurement condition including whether gestures instructed by the set of prompts being completed, a threshold amount of the video data obtained, the video data being of a threshold image quality, a waveform of the video data satisfying a threshold, and the body part in the video data being identified, segmented, and labeled;
second determining code configured to cause the at least one processor to determine, using a model, the UPDRS value based on the video data associated with the movement of the body part of the user; and
providing code configured to cause the at least one processor to, based on the measurement condition being satisfied, provide the UPDRS value, after determining the UPDRS value, to permit an evaluation of the user based on the UPDRS value.

9. The user device of claim 8, further comprising:
generating code configured to cause the at least one processor to generate sensor data based on the user of the user device manipulating the user device,
wherein the second determining code is further configured to cause the at least one processor to determine the UPDRS value based on the sensor data and the video data.

10. The user device of claim 8, wherein:
the second determining code is further configured to cause the at least one processor to determine a stage of Parkinson's disease for the user based on the video data, and
the providing code is further configured to cause the at least one processor to provide information that identifies the stage of Parkinson's disease.

11. The user device of claim 8, wherein the UPDRS value is a movement disorder society (MDS) UPDRS value.

12. The user device of claim 8, wherein the UPDRS value is at least one of a zero, one, two, three, or four.

13. The user device of claim 8, further comprising:
receiving code configured to cause the at least one processor to receive, from a server device, the model that is a deep neural network (DNN) model.

14. The user device of claim 8,
wherein the obtaining code is further configured to cause the at least one processor to obtain a plurality of pieces of video data based on providing the set of prompts.

15. A non-transitory computer-readable medium storing instructions, the instructions comprising: one or more instructions that, when executed by one or more processors of a user device for determining a unified Parkinson's disease rating scale (UPDRS) value associated with a user of the user device, cause the one or more processors to:
provide, via an output component of the user device, a set of prompts, each prompt instructing the user to perform a predefined gesture of a body part;
obtain video data associated with a movement of the body part of the user;
determine whether a measurement condition is satisfied, the measurement condition including whether gestures instructed by the set of prompts being completed, threshold amount of the video data obtained, the video data being of a threshold image quality, a waveform of the video data satisfying a threshold, and the body part in the video data being identified, segmented, and labeled;
based on the measurement condition being satisfied, determine, using a model, the UPDRS value based on the video data associated with the movement of the body part of the user; and
provide the UPDRS value, after determining the UPDRS value, to permit an evaluation of the user based on the UPDRS value.

16. The non-transitory computer-readable medium of claim 15, wherein the one or more instructions are further configured to cause the one or more processors to:
generate sensor data based on the user of the user device manipulating the user device; and
determine the UPDRS value based on the sensor data and the video data.

17. The non-transitory computer-readable medium of claim 15, wherein the one or more instructions are further configured to cause the one or more processors to:
determine a stage of Parkinson's disease for the user based on the video data; and
provide information that identifies the stage of Parkinson's disease.

18. The non-transitory computer-readable medium of claim 15, wherein the UPDRS value is a movement disorder society (MDS) UPDRS value.

19. The non-transitory computer-readable medium of claim 15, wherein the UPDRS value is at least one of a zero, one, two, three, or four.

20. The non-transitory computer-readable medium of claim 15, wherein the one or more instructions are further configured to cause the one or more processors to:
obtain a plurality of pieces of video data based on providing the set of prompts.

* * * * *